United States Patent [19]

Fujiwara

[11] Patent Number: 5,715,061
[45] Date of Patent: Feb. 3, 1998

[54] OPTICAL MEASURING APPARATUS AND OPTICAL MEASURING METHOD

[75] Inventor: Nariaki Fujiwara, Kyoto, Japan

[73] Assignee: Dainippon Screen Mfg. Co., Ltd., Japan

[21] Appl. No.: 746,576

[22] Filed: Nov. 14, 1996

[30] Foreign Application Priority Data

Nov. 14, 1995 [JP] Japan .................... 7-295420

[51] Int. Cl.$^6$ .................................... G01B 11/14
[52] U.S. Cl. ........................ 356/375; 250/559.29
[58] Field of Search ............... 250/559.27, 559.29; 356/73, 150, 375

[56] References Cited

U.S. PATENT DOCUMENTS

| | | | |
|---|---|---|---|
| 4,558,949 | 12/1985 | Uehara et al. | 356/375 |
| 4,844,617 | 7/1989 | Kelderman et al. | 356/381 |
| 4,864,123 | 9/1989 | Mizutani et al. | 250/559.27 |
| 5,120,966 | 6/1992 | Kondo | 356/381 |
| 5,202,744 | 4/1993 | Louis | 356/73 |
| 5,355,223 | 10/1994 | Magome | 356/381 |
| 5,483,079 | 1/1996 | Yonezawa | 250/559.29 |
| 5,510,892 | 4/1996 | Mizutani et al. | 356/375 |
| 5,530,237 | 6/1996 | Sato et al. | 356/381 |

*Primary Examiner*—Frank G. Font
*Assistant Examiner*—Zandra V. Smith
*Attorney, Agent, or Firm*—Ostrolenk, Faber, Gerb & Soffen, LLP

[57] ABSTRACT

In an apparatus for optically measuring a sample by irradiating the same with a measuring beam through first and second annular reflecting mirrors, a through hole is provided in the first reflecting mirror and a lens is arranged in such through hole. An irradiated position on the sample is irradiated with a detecting beam from a semiconductor laser through the lens. A photosensitive device is arranged on the rear surface of the first reflecting mirror, so that respective intensity distributions of a measuring beam and the detecting beam reflected at the irradiated position can be detected. The surface state and the position of the target sample at the irradiated position are determined from the intensity distributions of these beams. Thus, the reliability of the result of a measurement can be improved.

27 Claims, 11 Drawing Sheets

OPTICAL MEASURING APPARATUS AND OPTICAL MEASURING METHOD

BACKGROUND OF THE INVENTION

1. Field of the Invention

The present invention relates to an optical measuring apparatus and an optical measuring method for optically measuring a target sample by irradiating the same with a measuring beam from a measuring light source through a reflecting objective lens or the like.

2. Description of the Background Art

In a semiconductor integrated circuit device, various impurity diffusion regions, an insulating film, a wiring pattern and the like are formed on a major surface of a semiconductor wafer, as is well known in the art. Various types of noncontact optical measuring apparatuses are employed in order to measure formations. situations of these structures.

Such optical measuring apparatuses include, for example, a film thickness measuring apparatus for measuring the thickness of a thin film which is formed on a semiconductor wafer. In a conventional thickness measuring apparatus shown in FIG. 11, an illumination optical system 2 comprising a halogen lamp HL and a see-through type deuterium lamp DL is provided as a light source. An outgoing beam from the halogen lamp HL is temporarily condensed on a light emitting part of the deuterium lamp DL through a lens L, and thereafter passes through a field stop FS through an extra-axial ellipsoidal mirror EM. Thus, a measuring beam employed for measuring the film thickness is emitted from the illumination optical system 2 toward an imaging optical system 3.

This imaging optical system 3 comprises a reflecting objective lens RO and a half mirror HM, and the lens RO is formed by combining two reflecting mirrors RO1 and RO2. The reflecting mirror RO1 is an annular convex spherical mirror having an upper surface forming a mirror surface, and the reflecting mirror RO2 is an annular concave spherical mirror having a lower surface forming a mirror surface. These reflecting mirrors RO1 and RO2 form an optical system having an optical axis which is perpendicular to a plane on which a target sample SP is placed. The measuring beam going out from the field spot FS to be thereafter reflected by the half mirror HM is further reflected by the reflecting mirrors RO1 and RO2, to be applied onto a surface of the target sample SP which is placed on an image side focal plane of the reflecting objective lens RO. Thus, the target sample SP is illuminated. The measuring beam reflected by the surface of the target sample SP passes through the half mirror HM, to be thereafter condensed on the position of a plate PP which is provided on a spectroscopic unit 4.

The spectroscopic unit 4 is formed by the plate PP having a pinhole, a concave diffraction grating HG for separating reflected light passing through the plate PP into its spectral components, and a photodetector LIS for detecting each spectrum from the concave diffraction grating HG. The measuring beam reflected by the target sample SP and passed through the plate PP is separated into its spectral components by the concave diffraction grating HG, detected by the photodetector LIS as a spectral signal corresponding to the energy of each spectrum, and outputted toward a control unit (not shown).

This control unit calculates the actual spectral reflectance of the target sample on the basis of its spectral signal. Thereafter the control unit calculates the deviation between the actual spectral reflectance and a calibration curve spectral reflectance previously calculated for proper film thickness pitch determines a film thickness value having the minimum deviation, and displays the result on a CRT screen.

According to the optical measuring apparatus having the aforementioned structure, the film thickness on the target sample SP can be measured in a noncontact/nondestructive manner using a measuring beam having a wide wavelength region ranging from the ultraviolet to near infrared regions. In particular when the target sample SP is prepared by forming an ultrathin film such as a silicon oxide film of, for example, not more than 100 Å in thickness on a silicon substrate the signal-to-noise ratio of the detected signal can be improved by employing an ultraviolet wavelength beam, so that the thickness of the ultrathin film can be measured with high accuracy.

In making a thickness measurement of such an ultrathin film, inclination of the target sample SP remarkably influences the measured value. Thus, the inclination of the target sample SP is controlled in the film thickness measuring apparatus. In order to measure the ultrathin film (not more than 100 Å in thickness) provided on the silicon substrate it is necessary to control the semiconductor integrated circuit device (target sample) such that is not inclined. The target sample SP may be warped from annealing or the like during fabrication of semiconductor integrated circuit device, and hence it is necessary to detect whether or not the target sample SP is inclined in the thickness measurement.

Therefore, in order to detect the inclination of the target sample SP a detecting beam is applied to the surface of the target sample SP at a relatively shallow angle from the exterior of the film thickness measuring apparatus shown in FIG. 11 for receiving a reflected beam reflected by the target sample SP, thereby obtaining the inclination. When an apparatus for detecting the inclination is added to the exterior of the film thickness measuring apparatus, however, the film thickness measuring apparatus is disadvantageously increased in size. Since the detecting beam enters the target sample SP along an optical axis which is different from that of the film thickness measuring apparatus, it is difficult to adjust the incident position of the detecting beam to be aligned with the incident position (an irradiated position IP) of the measuring beam. For example, the detection result may be so varied with the surface state of the target sample SP that sufficient reliability cannot be attained due to a pattern edge which is present on the irradiated position IP.

A method for solving such problems is adapted to apply a measuring beam and a detecting beam to the same irradiated position IP along the same optical axis. If the direction of reflection of the detecting beam is detected by merely aligning the optical axes, however, the measuring and detecting beams cannot be effectively separated from each other when a pattern edge is present on the irradiated position IP or the surface of the target sample SP is coarse. Thus, the inclination of the target sample SP at the irradiated position IP receiving the measuring beam and the surface state such as surface roughness cannot be correctly detected.

If a pattern edge is present on the irradiated position IP, the direction of reflection of the detecting beam is partially changed on this pattern edge and the reflected detecting beam is partially eclipsed by the reflecting objective lens RO which causes a reduction in detection accuracy.

Thus, in general the surface state of the target sample SP at the irradiated position IP cannot be correctly detected and hence the film thickness is measured while the target sample SP is inclined, for example, disadvantageously leading to a reduction in reliability of the film thickness measurement.

Such a problem is not limited to the film thickness measuring apparatus, but is common to general optical measuring apparatuses for optically measuring target samples by irradiating the same with measuring beams through reflecting objective lenses.

SUMMARY OF THE INVENTION

The present invention is directed to an optical measuring apparatus for optically measuring a target sample such as a semiconductor integrated circuit and an optical measuring method employing this apparatus.

According to the present invention, the apparatus comprises a first light source for emitting a first beam, a first optical system having a first optical axis for guiding the first beam to an irradiated position on the sample, a second light source for emitting a second beam, a second optical system having a second optical axis for guiding the second beam to the irradiated position, the first and second axes being at least partially coaxial at the irradiated position, detecting means for detecting an intensity distribution of reflected light from the irradiated position, determination means for determining a surface state and a position of the sample at the irradiated position from the intensity distribution of the reflected light, and measuring means for acquiring measurement information from the sample in response to the result of the determination by the determination means.

According to an aspect of the present invention, the first optical system comprises an annular first reflecting mirror being arranged above the sample and having a convex spherical mirror surface and a back face being opposed to the sample, and a second reflecting mirror being arranged above the first reflecting mirror and having a concave spherical mirror surface being opposed to the sample. The second optical system comprises a lens being provided in a through hole formed at the center of the first reflecting mirror. The detecting means comprises an annular photosensitive device being arranged between the first reflecting mirror and the sample for receiving the reflected light. The first beam passes through a central hole of the second reflecting mirror, is reflected by the first reflecting mirror, and thereafter reflected by the second reflecting mirror again to be guided to the irradiated position. The second beam passes through the central hole of the second reflecting mirror and is thereafter transmitted through the lens to be guided to the irradiated position.

The inventive apparatus is employed for measuring, for example the thickness of a thin film which is formed on a surface of the sample.

Preferably, the second light source is a semiconductor laser.

The present invention is also directed to an optical measuring method which employs this apparatus.

Accordingly, an object of the present invention is to determine the surface state and the position (the spatial position where the sample is arranged and the orientation of the sample) of the sample, thereby improving reliability of the measurement result.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

<1. Overall Structure and Operation>

Figure 1:
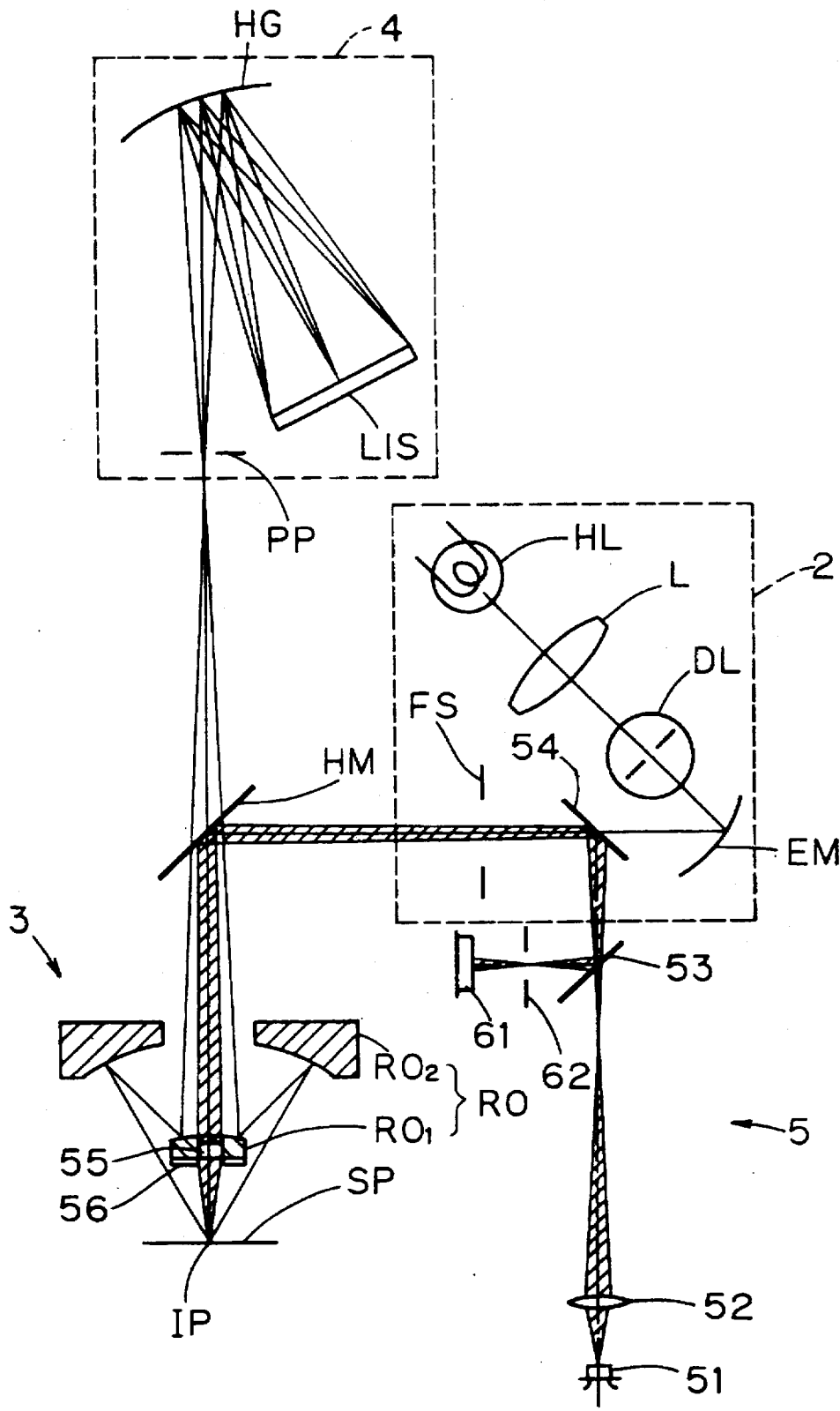
FIG. 1 illustrates the structure of an optical measuring apparatus according to a preferred embodiment of the present invention.
Figure 11:
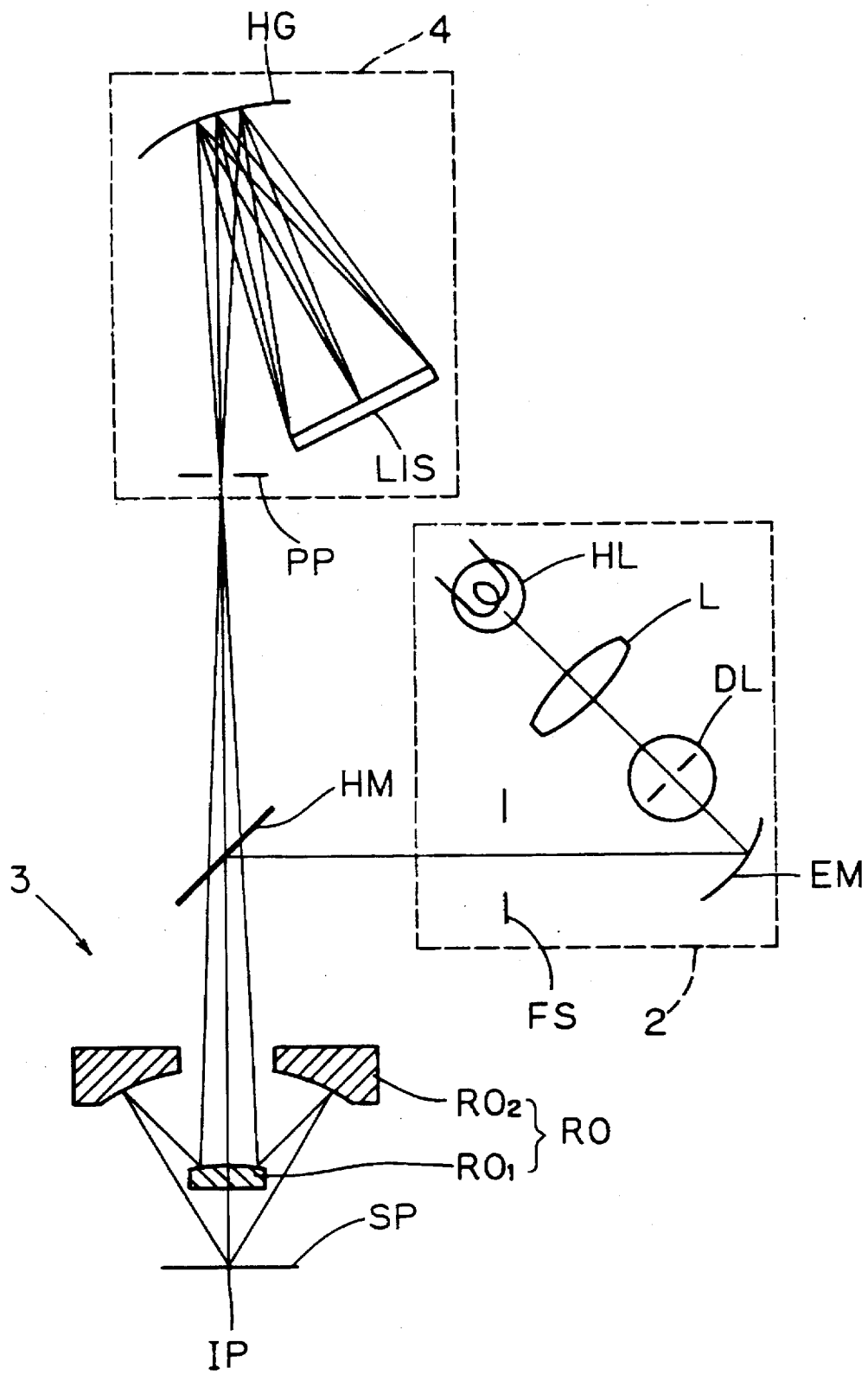
FIG. 11 illustrates a film thickness measuring apparatus which is an exemplary conventional optical measuring device.

FIG. 1 illustrates the structure of an apparatus for measuring the thickness of a film which is formed on a sample such as a semiconductor substrate, which is one optical measuring apparatus according to a preferred embodiment of the present invention. This optical measuring apparatus comprises an illumination optical system 2, an imaging optical system 3, a spectroscopic unit 4 and a surface state detecting unit 5. The inventive optical measuring apparatus is different from the prior art (FIG. 11) in that the surface state detecting unit 5 is added for detecting a surface state and a position (the spatial position where a sample is arranged and the orientation of the sample) of a target sample SP. The remaining structure of this embodiment is identical to that of the prior art, and hence identical elements are denoted by the same reference numerals to omit redundant description.

This surface state detecting unit 5 comprises a semiconductor laser (detecting light source) 51 for generating a detecting beam which is condensed on a position conjugate with the plate PP by a lens 52 and thereafter, through a half mirror 53, incident upon a half mirror 54 arranged on an optical path of a measuring beam. This half mirror 54 is arranged between an extra-axial ellipsoidal mirror EM and a field stop FS, for guiding the incident detecting beam to the half mirror HM through the same optical path as the measuring beam. The detecting beam which is incident upon the half mirror HM is further reflected toward the imaging optical system 3. Referring to FIG. 1, the detecting beam emitted from the semiconductor laser 51 is slantly hatched to be readily distinguished from the measuring beam.

Figure 2A:
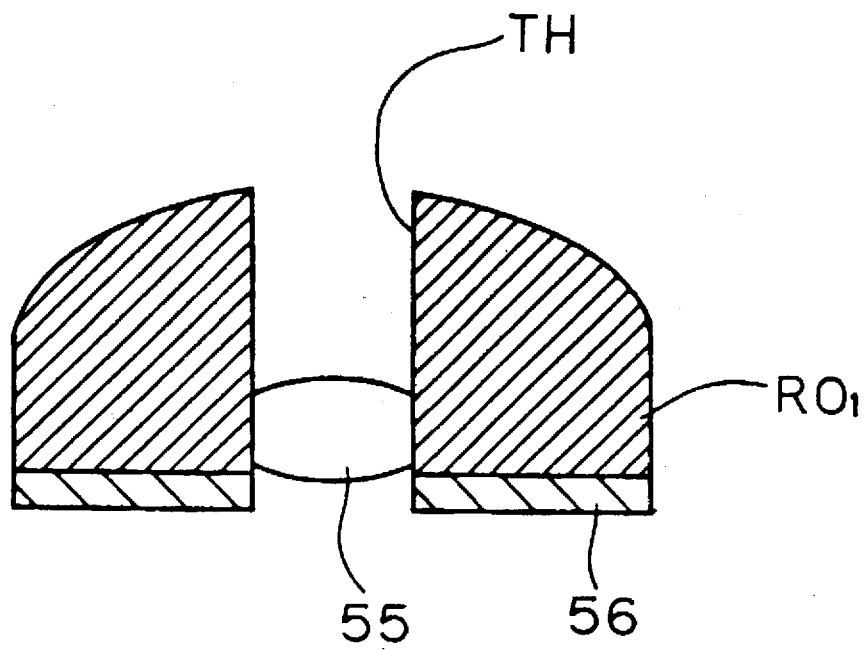
FIG. 2A-2B an enlarged sectional view showing a lens and a photosensitive device mounted on a reflecting mirror.
Figure 2B:
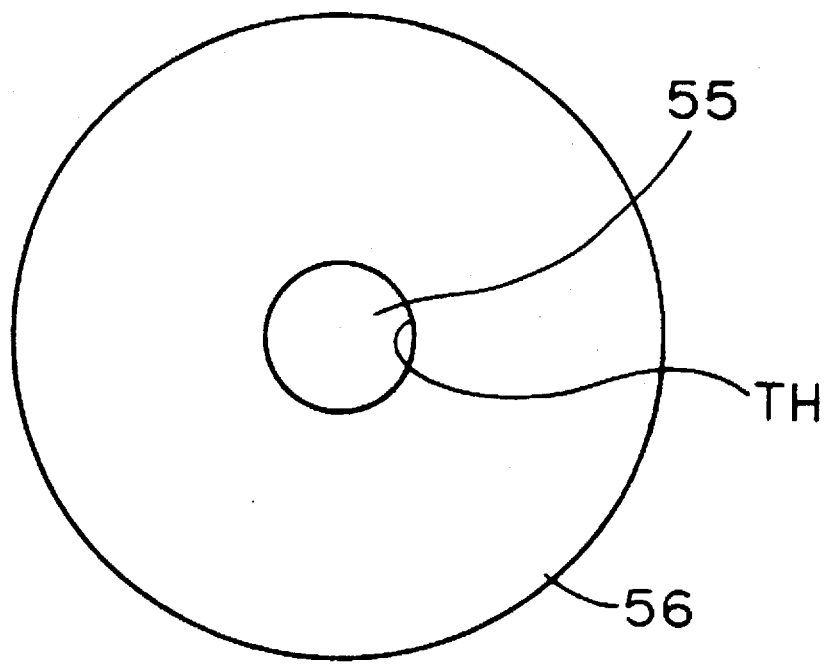

In this surface state detecting unit 5, a lens 55 is arranged in a through hole TH which is provided to pass through a first reflecting mirror RO1 along the optical path of the measuring and detecting beams, as shown in FIG. 2. Therefore, the detecting beam from the half mirror HM is incident upon the lens 55 through the through hole TH and applied to an irradiated position IP on a surface of the target sample SP, which is irradiated with the measuring beam by the lens 55.

Further, surface state detecting unit 5, an annular photosensitive device 56 serving as detecting means is mounted on a rear surface of the first reflecting mirror RO1 facing the target sample SP, for detecting intensity distribution(s) of the measuring beam and/or the detecting beam in response to the surface state and the position of the target sample SP at the irradiated position IP. The relation between the surface state and the position of the target sample SP at the irradiated position and the light intensity distribution(s) on the photosensitive device 56 is described later in detail.

Referring to FIG. 1, numeral 61 denotes a photoreceptor for receiving the detecting beam which is reflected by the target sample SP and passes through a pinhole of a plate 62 arranged on a position conjugate with the plate PP. This photoreceptor 61 is provided for focusing the target sample SP.

Figure 3:
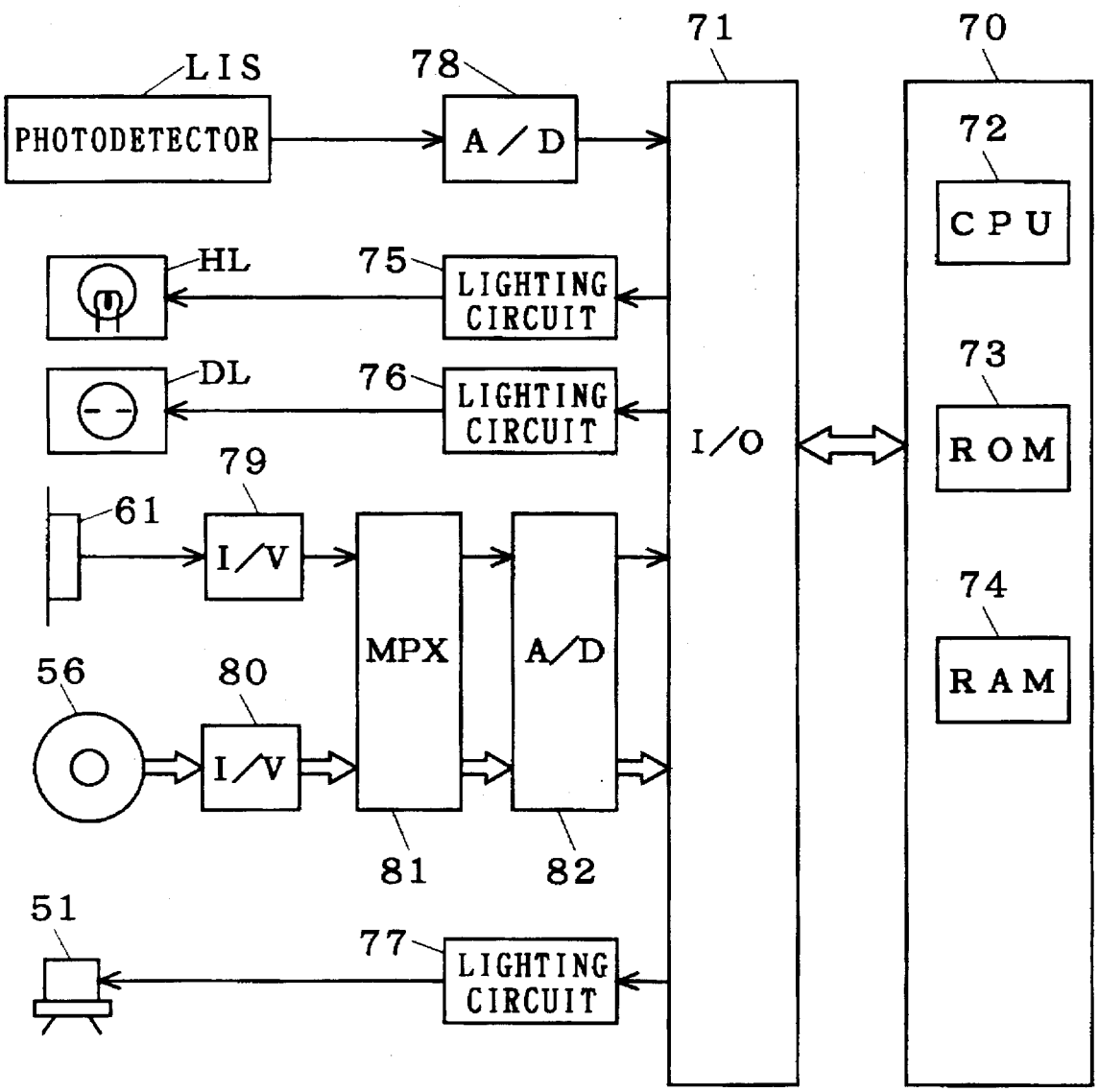
FIG. 3 is a block diagram showing the electrical structure of the optical measuring apparatus.

FIG. 3 is a block diagram showing the electrical structure of the optical measuring apparatus. This optical measuring apparatus comprises a computer 70 and an I/O port 71. The computer 70 has a CPU 72, a ROM 73 and a RAM 74, and performs control and operations described later.

Lighting circuits 75 to 77 are electrically connected to a halogen lamp HL, a deuterium lamp DL and the semiconductor laser 51 respectively. Lighting command signals for controlling lighting/turnoff of the halogen lamp HL, the deuterium lamp DL and the semiconductor laser 51 are generated by the computer 70 and supplied to the lighting circuits 75 to 77 respectively, whereby the halogen lamp HL, the deuterium lamp DL and the semiconductor laser 51 are lighted/turned off at timings described later respectively.

A photodetector LIS outputs a spectral signal corresponding to the energy of each spectrum, which signal is converted to a digital signal by an A-D converter 78 and thereafter incorporated in the computer 70. Output signals from the photosensitive device 56 and the photoreceptor 61 are converted to voltage signals by current-to-voltage converters 79 and 80, and thereafter incorporated in the computer 70 through a multiplexer 81 and an A-D converter 82.

The overall operation of the optical measuring apparatus having the aforementioned structure is now described. First, the halogen lamp HL, the deuterium lamp DL and the semiconductor laser 51 are lighted, in order to detect the surface state and the position of the target sample SP. Thus, the measuring and detecting beams are applied to a specific position (the irradiated position IP) of the target sample SP through a reflecting objective lens RO, and reflected by the irradiated position IP to return to the reflecting objective lens RO.

The measuring and detecting beams returning to the reflecting objective lens RO are incident upon the photodetector LIS or the photoreceptor 61 either without entering the photosensitive device 56 or partially incident upon the photosensitive device 56, in response to the surface state and the position of the target sample SP at the irradiated position IP. When the measuring and detecting beams are incident upon the photosensitive device 56, the intensity distributions of the former on the latter are varied with the surface state and the position of the target sample SP. Thus, it is possible to detect the surface state and the position of the target sample SP at the irradiated position IP by obtaining the intensity distributions of the measuring and detecting beams reflected by the target sample SP on the photosensitive device 56 respectively and checking the intensity distributions.

While it is better to independently obtain the intensity distributions of the measuring and detecting beams which are reflected by the target sample SP as described above in order to reliably detect the surface state and the position of the target sample SP, the reflected beams must be separated from each other since these beams partially overlap with each other in the optical measuring apparatus having the aforementioned structure. In this embodiment, the lighting circuit 77 supplies a pulse signal for periodically changing (modulating) only the detecting beam outgoing from the semiconductor laser 51. Thus, the unmodulated measuring beam and the modulated detecting beam can be clearly separated from each other, to that the intensity distributions thereof can be obtained independently of each other.

<2. Method of Detecting Surface State and Position of Target Sample SP>

The relations between the intensity distributions of the measuring and detecting beams independently obtained at the photosensitive device 56 as described above and the surface state and the position of the target sample SP at the irradiated position IP are now described in relation to three cases.

<2.1 When the Sample Surface is in a Horizontal State at the Irradiated Position IP>

Figure 4:
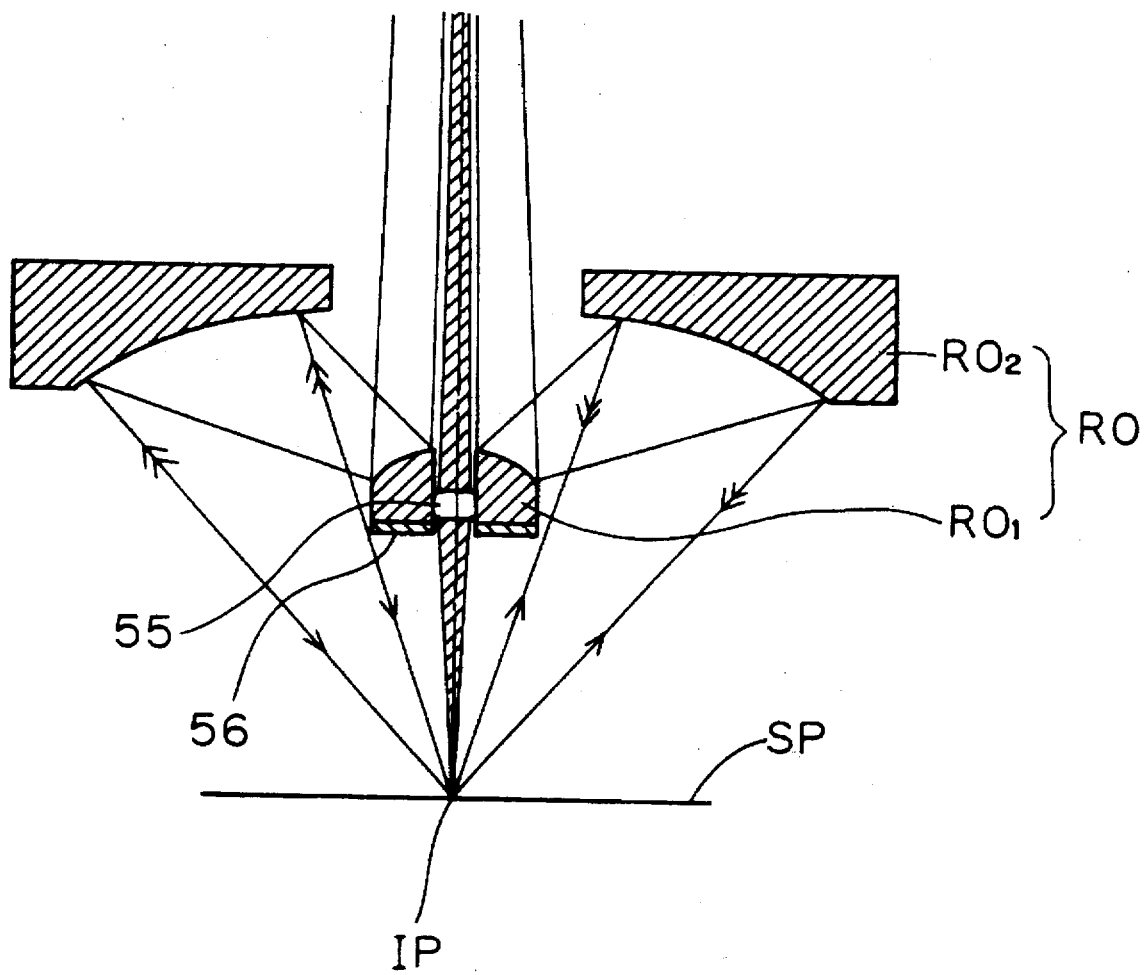
FIG. 4 illustrates how measuring and detecting beams advance when a surface of a target sample is in a horizontal state and in focus at an irradiated position.

When the surface of the target sample SP is in a horizontal state at the irradiated position IP and in focus (FIG. 4), the detecting beam (slantly hatched in FIG. 4) which is applied to the target sample SP through the lens 55 is reflected by the surface of the target sample SP, and returns to the lens 55 through the same path. Therefore, the detecting beam is not in the least incident upon the photosensitive device 56, and its intensity distribution at the photosensitive device 56 is zero over the entire surface. Further, the measuring beam, which advances through paths shown by the arrows in FIG. 4, is not in the least incident upon the photosensitive device 56 either, and its intensity distribution at the photosensitive device 56 is also zero over the entire surface.

Figure 5:
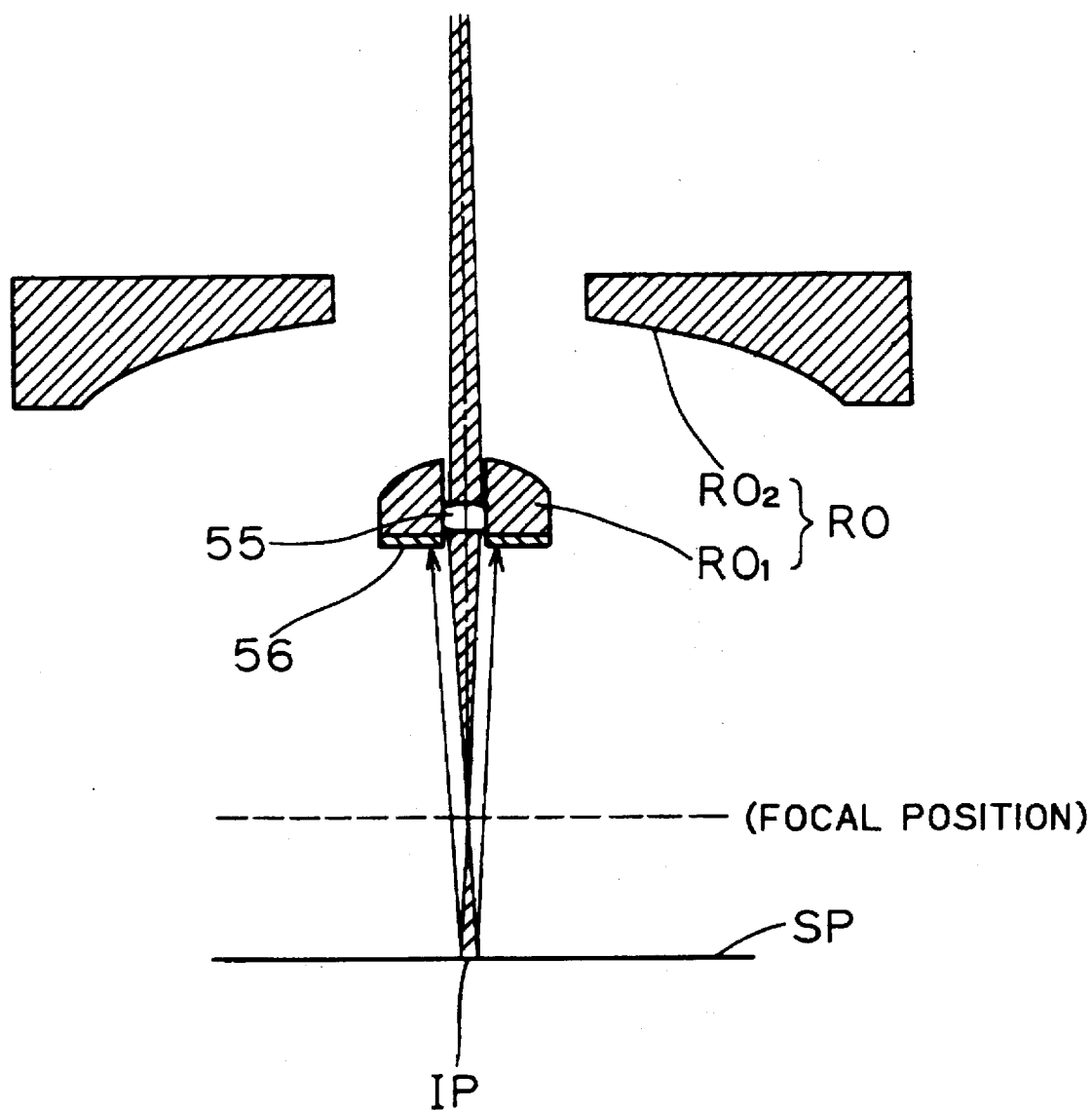
FIG. 5 illustrates how the detecting beam advances when the surface of the target sample is in a horizontal state and out of focus at the irradiated position.
Figure 6:
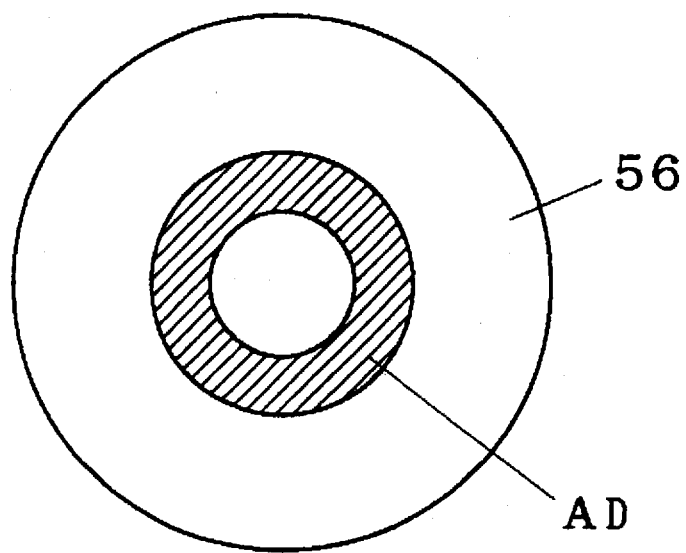
FIG. 6 typically illustrates how the detecting beam enters the photosensitive device when the surface of the target sample is in a horizontal state and out of focus at the irradiated position.

When the surface of the target sample SP is in a horizontal state at the irradiated position IP and is out of focus (FIG. 5), the detecting beam (slantly hatched in FIG. 5) which is applied to the target sample SP through the lens 55 is reflected by the surface of the target sample SP and returns to the lens 55 through a path which is different from that of incidence. Therefore, the detecting beam is introduced onto in incidence, to be introduced into the photosensitive device 56 as a beam which is concentric with and wider than the through hole TH. Therefore, the intensity distribution of the detecting beam corresponds to a concentric annular region AD at the photosensitive device 56 as shown in FIG. 5, so that a signal related thereto is outputted from the photosensitive device 56 and incorporated in the computer 70.

While the target sample SP is located under a focal position (shown by a broken line in FIG. 5) in this embodiment, the above description also applies to a target sample which is located above such a focal position.

As hereinabove described, the intensity distribution of the detecting beam at the photosensitive device 56 is either zero on the overall surface or is in the form of an annulus which is concentric with the through hole TH, whereby it is possible to determine whether or not the surface of the target sample SP is in a horizontal state at the irradiated position IP using the computer 70 to interpret the output signal from the photosensitive device 56.

<2.2 When the Sample Surface is Inclined at the Irradiated Position IP>

When the surface of the target sample SP is inclined at the irradiated position IP due to an inclination of the overall target sample SP or the like, both the measuring and detecting beams reflected by the target sample SP enter the photosensitive device 56. The cases of the measuring and detecting beams are now described independently of each other.

Figure 7:
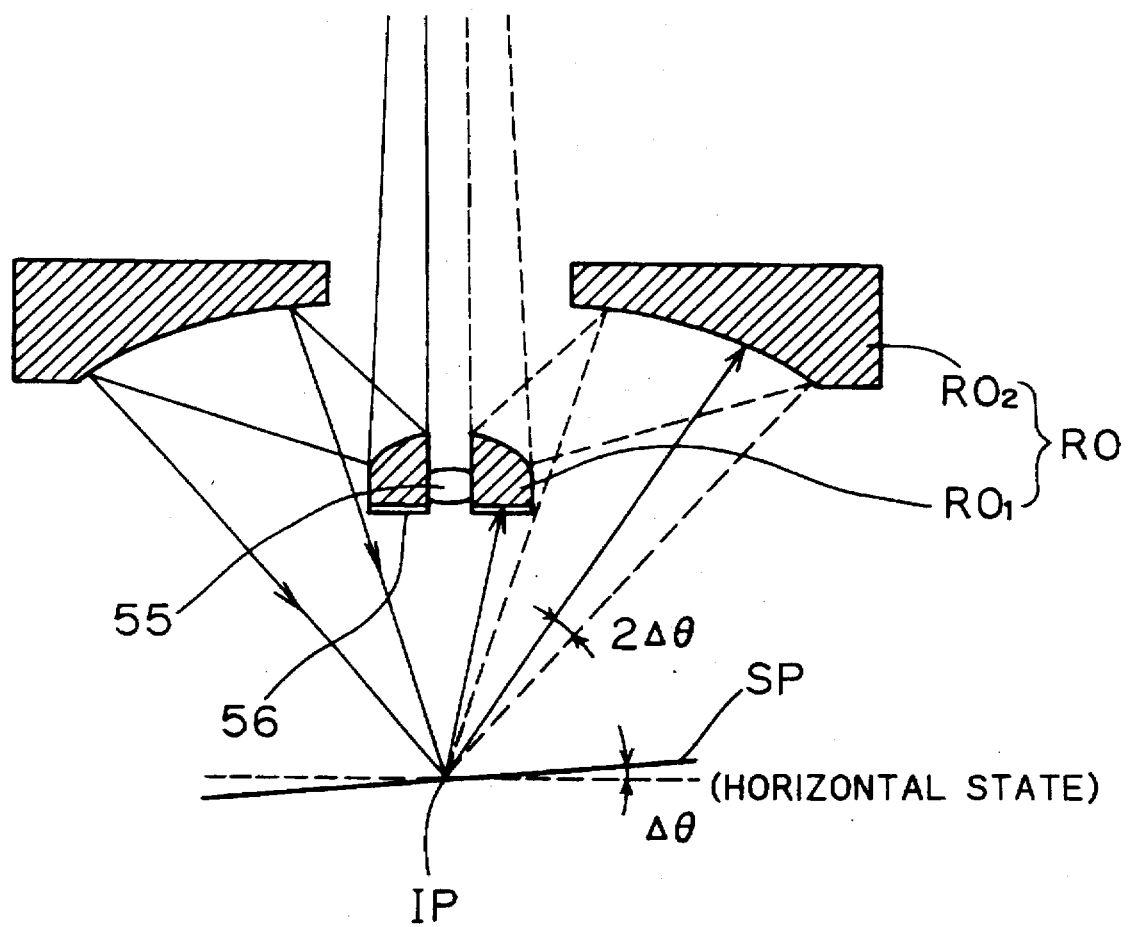
FIG. 7 illustrates how the measuring beam advances when the surface of the target sample is inclined at the irradiated position.

FIG. 7 illustrates how the measuring beam advances when the sample surface is inclined at the irradiated position IP. For clarity, FIG. 7 only partially shows the measuring beam and illustrates the optical path of the measuring beam for the sample surface which is not inclined at the irradiated position IP as described above in broken lines. When the surface of the target sample SP is inclined from a horizontal state by an angle $\Delta\theta$ at the irradiated position IP as shown in FIG. 7, the measuring beam which is reflected by the surface of the target sample SP deviates by an angle $2\Delta\theta$ in the same direction as that of the inclination of the target sample SP. Therefore, the reflected measuring beam is partially applied to the photosensitive device 56, such that the intensity distribution of the measuring beam corresponds to a crescent region AM at the photosensitive device 56 as shown in FIG. 8, and a signal related thereto is outputted from the photosensitive device 56 and incorporated in the computer 70.

Figure 8:
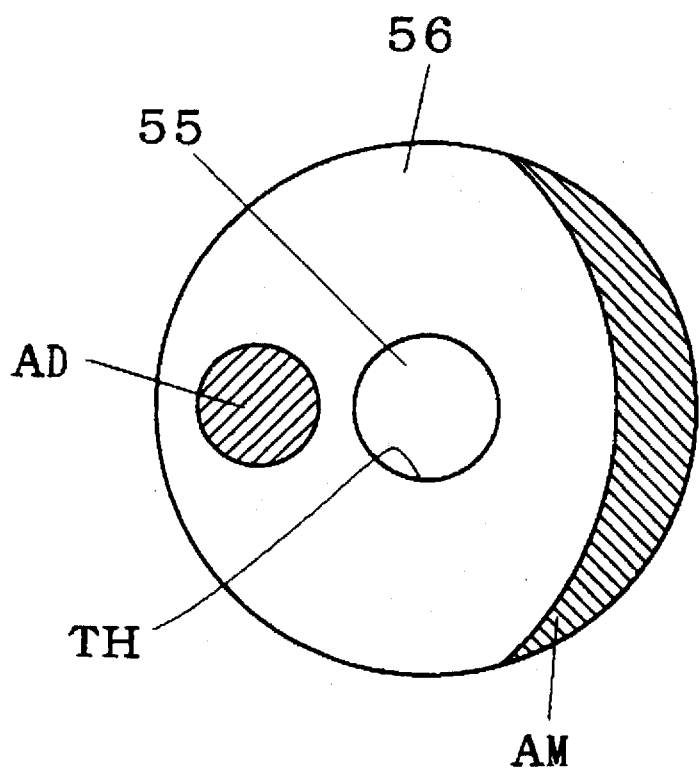
FIG. 8 typically illustrates how the measuring and detecting beams enter the photosensitive device when the surface of the target sample is inclined at the irradiated position.
Figure 9:
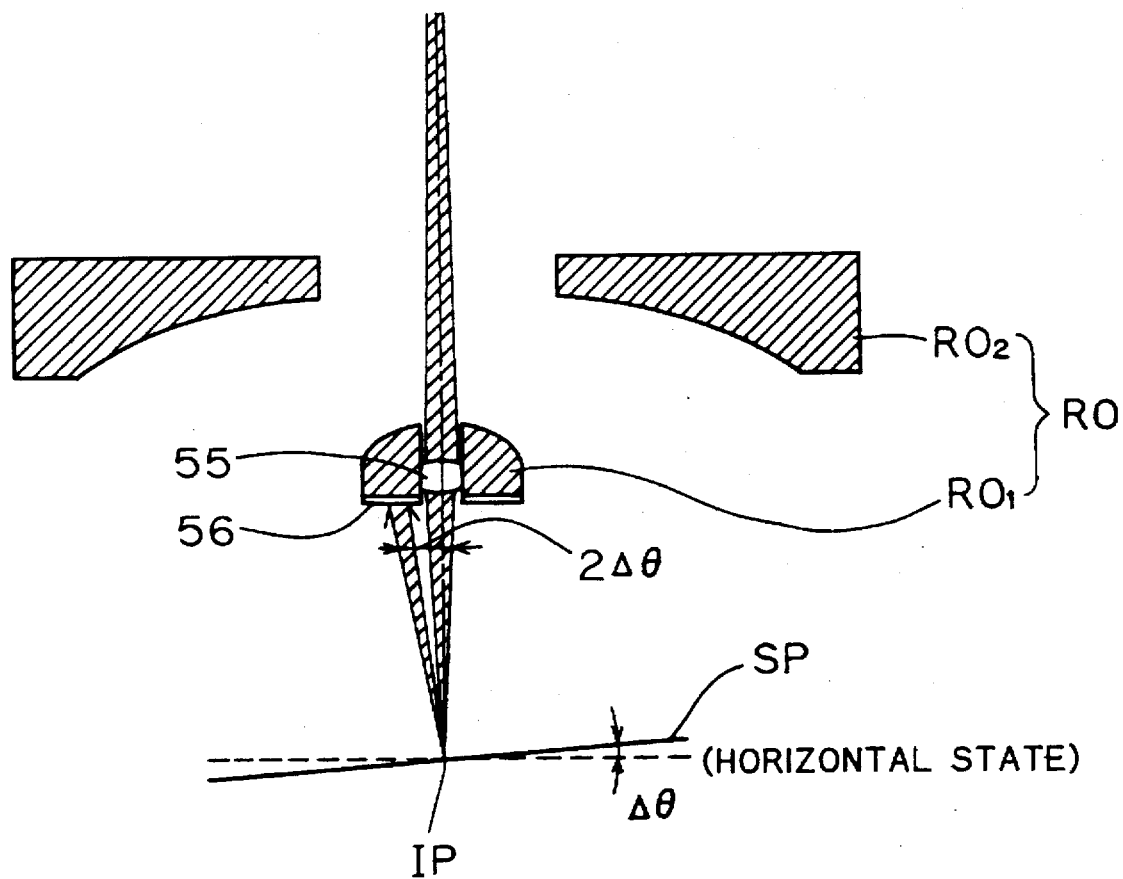
FIG. 9 illustrates how the detecting beam advances when the surface of the target sample is inclined at the irradiated position.

FIG. 9 illustrates how the detecting beam advances when the sample surface is inclined at the irradiated position IP. When the surface of the target sample SP is inclined from a horizontal state by an angle $\Delta\theta$ at the irradiated position IP as shown in FIG. 9, the detecting beam which is reflected by the surface of the target sample SP deviates by an angle $2\Delta\theta$ in the same direction as that of the inclination of the target sample SP in a similar way as the measuring beam. Therefore, the reflected detecting beam does not return to the lens 55, but enters the photosensitive device 56. Therefore, a spot of the detecting beam is formed on the photosensitive device 56 as shown in FIG. 8, which intensity distribution of the corresponds to the annular region AD at the photosensitive device 56, and a signal related thereto is outputted from the photosensitive device 56 and incorporated in the computer 70.

The positions of incidence of the measuring and detecting beams upon the photosensitive device 56 are opposite to each other about the center, as shown in FIG. 8.

As hereinabove described, the intensity distributions of the measuring and detecting beams appear in opposite directions about the center of the photosensitive device 56 when the surface of the target sample SP is inclined at the irradiated position IP, whereby it is possible to determine whether or not the surface of the target sample SP is inclined at the irradiated position IP using the computer 70 to interpret the output signal from the photosensitive device 56.

<2.3 When a Pattern Ege is Present on the Irradiated Position IP or the Target Sample has a Coarse Surface>

Figure 10:
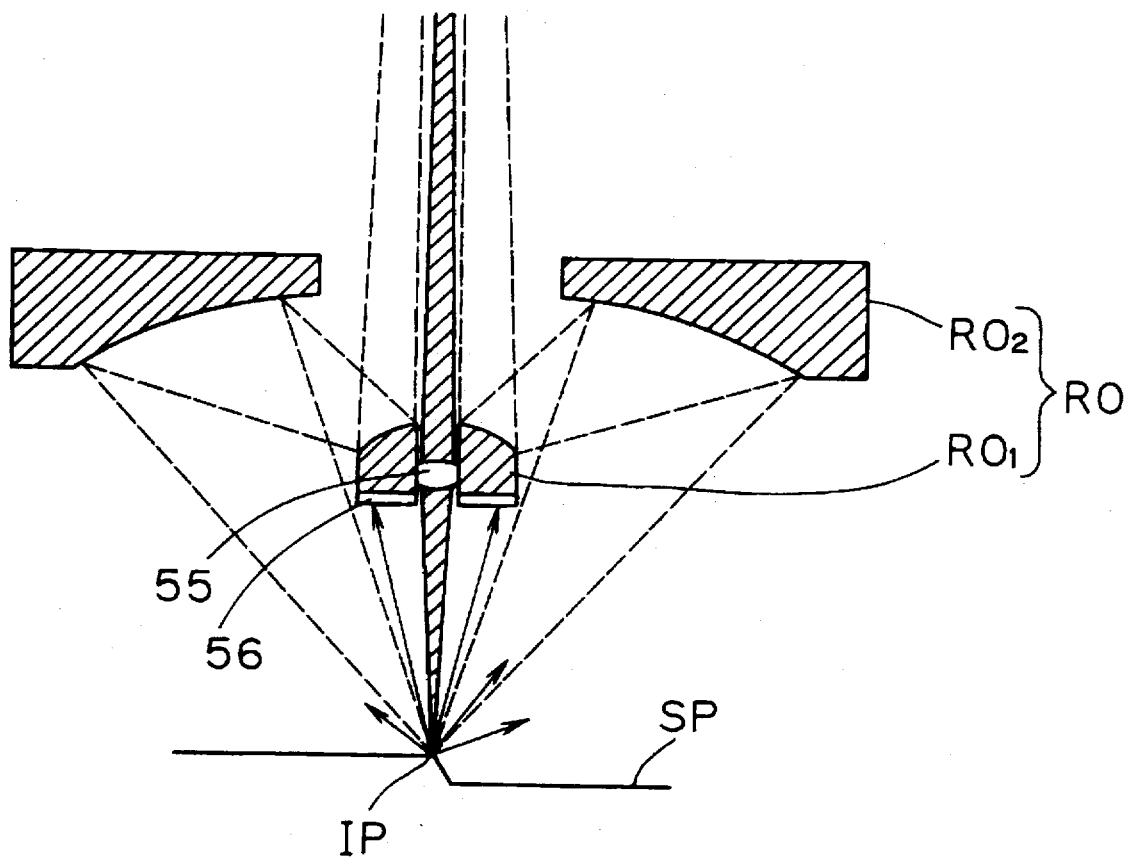
FIG. 10 illustrates how the measuring and detecting beams advance when a pattern edge is present on the irradiated position.

FIG. 10 illustrates how the measuring and detecting beams advance when a pattern edge is present on the irradiated position IP. When a pattern edge is present on the irradiated position IP as shown in FIG. 10, the measuring and detecting beams entering the irradiated position IP are scattered by the pattern edge, and the scattered beams partially enter the overall surface of the photosensitive device 56. Therefore, the intensity distributions of the measuring and detecting beams are feeble and substantially homogeneous along the overall surface of the photosensitive device 56, and a signal related thereto is outputted from the photosensitive device 56 and incorporated in the computer 70.

Also when the surface of the target sample SP at the irradiated position IP is coarse, the measuring and detecting beams entering the irradiated position IP are scattered by the sample surface in a similar manner as the aforementioned case where the pattern edge is present at the irradiated position, so that the scattered beams partially enter the overall surface of the photosensitive device 56. Therefore, the intensity distributions of the measuring and detecting beams are feeble along the overall surface of the photosensitive device 56 and substantially homogeneous, and a signal related thereto is outputted from the photosensitive device 56 and incorporated in the computer 70.

Thus, the intensity distributions of the measuring and detecting beams at the photosensitive device 56 are homogeneous substantially along the overall surface when a pattern edge is present on the irradiated position IP or the sample surface is coarse at the irradiated position IP, whereby it is possible to determine that a pattern edge is present on the irradiated position IP or the surface of the target sample SP at the irradiated position is coarse using the computer 70 to interpret the output signal from the photosensitive device 56.

In the optical measuring apparatus according to this embodiment, as hereinabove described, the through hole TH is provided in the first reflecting mirror RO1 so that the detecting beam is applied to the irradiated position IP through the lens 55 which is arranged in this through hole TH, whereby the measuring and detecting beams are applied to the same irradiated position IP through the same optical axis so that the apparatus can be miniaturized and the position of the target sample at the irradiated position can be detected with high reliability. Further, the intensity distributions of the measuring and detecting beams reflected by the surface of the target sample SP are obtained by the photosensitive device 56 which is mounted on the rear surface of the first reflecting mirror RO1 so that the surface state of the target sample SP at the irradiated position IP is detected from the states of the distributions, whereby it is possible to correctly detect that a pattern edge is present on the irradiated position IP or that the surface of the target sample SP is coarse.

<3. Operation after Detection of Surface State and Position of Target Sample SP>

A description is now made of the operation of the optical measuring apparatus after the detection of the surface state and the position of the target sample SP. After the surface state and the position of the target sample SP at the irradiated position IP are correctly detected in the aforementioned manner, the following process is performed in response to the results of the detection: When it is determined that/he sample surface is inclined at the irradiated position, a pattern edge is present at the irradiated position or the surface is coarse in the aforementioned manner, the computer 70 does not execute an actual measurement (film thickness measurement) but displays the surface state and the position of the target sample SP on a CRT screen (not shown) to inform the operator, and stops the measurement process of the irradiated position. When it is determined that the sample surface is in a horizontal state at the irradiated position IP and the surface state is good for measuring, the semiconductor laser 51 is turned off, the measuring beam from the halogen lamp HL and the deuterium lamp DL is applied to the irradiated position IP, and the beam reflected by the surface of the target sample SP is separated into its spectral components by the concave diffraction grating HG, so that a spectral signal corresponding to the energy of each spectrum is detected by the photodetector LIS. The output signal is incorporated in the computer 70 through the A-D converter 78 so that actual spectral reflectance of the target sample SP is calculated and the deviation between the actual spectral reflectance and the calibration curve spectral reflectance previously calculated for proper film thickness pitch for obtaining the thickness value having the minimum deviation and displaying the result on the CRT screen.

Thus, the surface state and the position of the target sample SP are detected in advance of the actual measurement so that the actual measurement is performed only when the surface state and the position are satisfactory, whereby measurement reliability can be improved.

While the photosensitive device 56 is mounted on the rear surface of the first reflecting mirror RO1 in this embodiment, the arrangement of the photosensitive device 56 is not restricted to this but an affect similar to that of this embodiment can be attained by arranging the photosensitive device 56 at an arbitrary position between the first reflecting mirror RO1 and the target sample SP.

While not only the beam in the wavelength region of the detecting beam but beams of other wavelength regions may pass through the through hole TH. However, a bandpass filter for transmitting only the beam of the wavelength region of the detecting beam can be arranged in the through hole TH or a wavelength region deviating from that of the measuring beam can be selected as the wavelength for the detecting beam, in order to allow passage of only a beam of a specific wavelength region (that of the detecting beam).

While the photoreceptor 61 is employed for focusing the target sample SP in this embodiment, the focusing method is not restricted thereto. In particular a method of imaging the detecting beam on a position conjugate with the surface of the target sample SP and detecting a position minimizing the beam diameter of the detecting beam thereby detecting the focal position or astigmatic focusing combined with a cylindrical lens can alternatively be employed.

While the photosensitive device 56 is employed in this embodiment, any device may alternatively be employed so far as the same can detect intensity distributions of light.

While the optical measuring apparatus has been described with reference to the apparatus (film thickness measuring apparatus) for measuring the film thickness of the target sample SP in this embodiment, the present invention is also applicable to an optical measuring apparatus other than the film thickness measuring apparatus.

While the invention has been shown and described in detail, the foregoing description is in all aspects illustrative and not restrictive. It is therefore understood that numerous modifications and variations can be devised without departing from the scope of the invention.

What is claimed is:

1. An optical measuring apparatus for optically measuring a sample, comprising:
    a first light source for emitting a first beam;
    a first optical system having a first optical axis for guiding said first beam to an irradiated position on said sample, said first optical system including an annular first reflecting mirror being arranged above said sample and having a convex spherical mirror surface on one face and a back face being opposed to said sample, and a second reflecting mirror being arranged above said first reflecting mirror and having a concave spherical mirror surface being opposed to said sample;
    a second light source for emitting a second beam;
    a second optical system having a second optical axis for guiding said second beam to said irradiated position, said first and second axes being at least partially coaxial at said irradiated position, said second optical system including a lens located in a through hole which is disposed in the center of said first reflecting mirror;
    a detecting unit for detecting an intensity distribution of reflected light from said irradiated position, said detecting unit including an annular photosensitive device being arranged between said first reflecting mirror and said sample for receiving said reflected light;
    a determination unit for determining a surface state and a position of said sample at said irradiated position from said intensity distribution of said reflected light; and
    a measuring unit for acquiring measurement information from said sample in response to a result from said determination unit,
    said first beam passing through a central hole of said second reflecting mirror, being reflected by said first reflecting mirror and thereafter being reflected by said second reflecting mirror to said irradiated position; and
    said second beam passing through said central hole of said second reflecting mirror and being thereafter transmitted through said lens to said irradiated position.

2. The optical measuring apparatus in accordance with claim 1, wherein said second optical axis is perpendicular to a plane on which said sample is placed.

3. The optical measuring apparatus in accordance with claim 1, wherein:
    said second light source comprises a modulation unit for periodically changing the radiant intensity of said second beam; and
    said detecting unit further comprises a processing unit for extracting the intensity distributions of first and second components of said first and second beams respectively from said intensity distribution of said reflected light.

4. The optical measuring apparatus in accordance with claim 3, wherein said determination unit comprises a system for determining said surface state of said sample and whether said sample is horizontally positioned from said intensity distribution of said first component.

5. The optical measuring apparatus in accordance with claim 3, wherein said determination unit comprises a system for determining whether or not said sample is horizontally positioned from said intensity distribution of said second component.

6. The optical measuring apparatus in accordance with claim 3, wherein said determination unit comprises a system for determining whether or not said sample is in a prescribed measuring position from said intensity distribution of said component.

7. The optical measuring apparatus in accordance with claim 1, wherein said first light source includes a halogen lamp and a deuterium lamp.

8. The optical measuring apparatus in accordance with claim 1, wherein said second light source includes a semiconductor laser.

9. The optical measuring apparatus in accordance with claim 1, wherein said first optical axis is perpendicular to a plane on which said sample is placed.

10. A method for optically measuring a sample, comprising:
   a) a first irradiation step of applying a first beam along a first optical axis to an irradiated position on said sample;
   a-1) a step of reflecting said first beam off of an annular first reflecting mirror disposed above said sample and having a convex spherical mirror surface on one face and a back face being opposed to said sample;
   a-2) a step of reflecting said first beam which is reflected by said first reflecting mirror off of a second reflecting mirror disposed above said first reflecting mirror and having a convex spherical mirror surface being opposed to said sample, said second reflecting mirror guiding said first beam to said irradiated position;
   b) a second irradiation step of applying a second beam along a second optical axis to said irradiated position, said first and second axes being at least partially coaxial at said irradiated position;
   b-1) a step of transmitting said second beam through a lens located in a through hole which is disposed in the center of said first reflecting mirror and guiding said second beam to said irradiated position;
   c) a detection step of detecting an intensity distribution of reflected light from said irradiated position;
   d) a determination step of determining a surface state and a position of said sample at said irradiated position from said intensity distribution of said reflected light; and
   e) a measuring step of acquiring measurement information from said sample in response to the result of said determination step.

11. The optical measuring method in accordance with claim 10, wherein said detection step comprises:
   c-1) a step of detecting an intensity distribution of reflected light from said irradiated position through an annular photosensitive device being arranged between said sample and said first reflecting mirror.

12. The optical measuring method in accordance with claim 11, wherein said second irradiation step comprises:
   b-3) a step of periodically changing a radiant intensity of said second beam, and said detection step further comprises:
   c-2) a step of extracting intensity distributions of first and second components of said first and second beams respectively from said intensity distribution of said reflected light.

13. The optical measuring method in accordance with claim 12, wherein said determination step comprises:
   d-1) a step of determining said surface state of said sample and whether or not said sample is horizontally positioned from said intensity distribution of said first component.

14. The optical measuring method in accordance with claim 12, wherein said determination step comprises:
   d-2) a step of determining whether or not said sample is horizontally positioned from said intensity distribution of said second component.

15. The optical measuring method in accordance with claim 12, wherein said determination step comprises:
   d-3) a step of determining whether or not said sample is in a measuring position from said intensity distribution of said second component.

16. The optical measuring method in accordance with claim 10, wherein said measuring step comprises:
   e-1) a step of measuring said sample only when said result of said determination indicates a measurable state.

17. The optical measuring method in accordance with claim 10, wherein said second irradiation step comprises a step of introducing said second beam perpendicularly to a plane in which said sample is place.

18. An optical measuring apparatus for measuring a sample, comprising:
   a first light source adapted to propagate a first beam of light along a first axis onto at least a portion of said sample;
   a second light source adapted to propagate a second beam of light along a second axis onto said portion of said sample, said first and second axis being at least partially coaxial at said portion of said sample;
   a first annular reflecting mirror having an aperture therethrough and first and second sides, said second side facing said sample; and
   a detecting unit for detecting an intensity distribution of reflected light from said portion of said sample, said detecting unit including a photosensitive device disposed between said second side and said sample.

19. The optical measuring apparatus of claim 18 further comprising a lens disposed in said aperture.

20. The optical measuring apparatus of claim 18 further comprising a second annular reflecting mirror having an aperture therethrough and a concave spherical mirror surface disposed on one side thereof, said concave spherical surface facing said sample, wherein said first annular reflecting mirror includes a convex spherical mirror surface disposed on said first side thereof, said convex spherical mirror surface facing said concave spherical surface.

21. The optical measuring apparatus of claim 20, wherein said first beam of light passes through said aperture of said second mirror, reflects off of said convex mirror of said first mirror and reflects off of said concave mirror of said second mirror onto said sample.

22. The optical measuring apparatus of claim 18 further comprising a modulation unit for intermittently changing an intensity of said second beam of light.

23. The optical measuring apparatus of claim 22, wherein said detecting unit extracts first and second intensity distributions corresponding to said first and second beams of light respectively.

24. The optical measuring apparatus of claim 23 further comprising a determination unit for determining at least one of a surface state, a position and an orientation of said sample from said intensity distribution of reflected light.

25. The optical measuring apparatus of claim 24, wherein said determination unit determines whether or not said sample is in a perpendicular orientation to at least one of said first and second axis using said first intensity distribution.

26. The optical measuring apparatus of claim 24 wherein said determination unit determines whether or not said sample is in a perpendicular orientation to at least one of said first and second axis using said second intensity distribution.

27. The optical measuring apparatus of claim 24 wherein, said determination unit determines whether or not said sample is at a proper focal position using said second intensity distribution.

* * * * *